(12) United States Patent
Patterson et al.

(10) Patent No.: US 6,533,766 B1
(45) Date of Patent: Mar. 18, 2003

(54) COATING MEDICAL DEVICE SURFACES FOR DELIVERING GAS-SUPERSATURATED FLUIDS

(75) Inventors: William R. Patterson, Irvine, CA (US); Jeffrey L. Creech, Marina Del Rey, CA (US)

(73) Assignee: TherOx, Inc., Irvine, CA (US)

( * ) Notice: Subject to any disclaimer, the term of this patent is extended or adjusted under 35 U.S.C. 154(b) by 0 days.

(21) Appl. No.: 09/466,626

(22) Filed: Dec. 17, 1999

Related U.S. Application Data

(63) Continuation-in-part of application No. 09/122,143, filed on Jul. 24, 1998, now Pat. No. 6,180,059.

(51) Int. Cl.[7] .............................................. A61M 31/00
(52) U.S. Cl. ..................................... 604/500; 427/2.12
(58) Field of Search ................................. 604/264, 265, 604/266, 267, 268, 269, 48, 19, 93.01, 500; 427/2.1, 2.12, 2.3

(56) References Cited

U.S. PATENT DOCUMENTS

| | | | |
|---|---|---|---|
| 4,265,927 A | * 5/1981 | Ericksson et al. | 427/2.24 |
| 5,047,020 A | * 9/1991 | Hsu | 604/266 |
| 5,541,167 A | 7/1996 | Hsu et al. | 514/56 |
| 5,928,916 A | 7/1999 | Keogh | 435/174 |
| 5,955,588 A | 9/1999 | Tsang et al. | 536/21 |
| 5,976,119 A | * 11/1999 | Spears et al. | 604/508 |
| 6,033,719 A | * 3/2000 | Keogh | 427/2.12 |
| 6,180,059 B1 | * 1/2001 | Divino, Jr. et al. | 422/45 |

FOREIGN PATENT DOCUMENTS

| | | | | |
|---|---|---|---|---|
| EP | 0 769 503 A2 | 4/1997 | | 37/10 |

* cited by examiner

*Primary Examiner*—Manuel Mendez
*Assistant Examiner*—Mark Han
(74) *Attorney, Agent, or Firm*—Margaret A. Kivinski

(57) ABSTRACT

A method is provided of using biocompatible surface-active agents to impart improved characteristics to a surface contacting a gas-supersaturated fluid, advantageously by forming on the surface a coating including an adsorbed biocompatible surface-active agent promoting surface charge neutralization or surface energy reduction, and of providing a surface contacting a gas-supersaturated fluid, the surface having such improved characteristics.

31 Claims, No Drawings

COATING MEDICAL DEVICE SURFACES FOR DELIVERING GAS-SUPERSATURATED FLUIDS

RELATED APPLICATIONS

This application is a continuation-in-part of U.S. patent application Ser. No. 09/122,143, which issued on Jan. 30, 2001 as U.S. Pat. No. 6,180,059B1, for "Method for the Preparation and Delivery of Gas-Enriched Fluids" by Divino, Jr. et al. filed Jul. 24, 1998, which is incorporated herein by reference.

FIELD OF THE INVENTION

The present invention relates generally to the coating of medical device surfaces contacting gas-enriched fluids, and more particularly, to the coating of medical device surfaces forming fluid conduits (e.g., catheters, infusion guidewires, tubing, capillaries and the like) to impart improved characteristics to the surfaces contacting oxygen-supersaturated fluids during delivery.

BACKGROUND OF THE INVENTION

This section is intended to introduce the reader to various aspects of art that may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Adverse biological reactions, such as thrombosis, inflammation and infection, are thought to result from tissues and fluids contacting or otherwise interacting with the surfaces of medical devices. Thus, for many years, there has been significant interest on the part of physicians and the medical industry to develop, manufacture and use clinically medical devices that do not tend to promote adverse biological reactions.

As described in U.S. Pat. No. 5,928,916, for example, one approach used for minimizing adverse biological reactions has been to attach various biomolecules to the surfaces of medical devices. Numerous attachment methods, such as covalent attachment techniques and ionic attachment techniques, have been used or suggested. Such attachment methods may involve the use of coupling agents to attach biomolecules to surfaces.

Heparin is a type of biomolecule often coupled to surfaces. Surface heparinization is thought to improve the thromboresistance of biomaterials and inhibit blood coagulation. The '916 patent describes, inter alia, some of the history of surface heparinization development and some of the methods for attaching heparin to surfaces. There are many approaches to binding heparin to biomaterial surfaces, and while methods of surface heparinization to minimize certain undesirable biological reactions are known, heparin continues to be of interest in the development of non-thrombogenic blood-contact biomaterial surfaces.

SUMMARY OF THE INVENTION

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

While biomolecules such as heparin have been used on surfaces to inhibit adverse biological reactions, one aspect of the present invention relates to methods using biomolecules to impart improved characteristics to medical device surfaces contacting gas-supersaturated fluids. More generally, one aspect of the present invention relates to methods using a biocompatible surface-active agent to impart improved characteristics to medical device surfaces contacting gas-supersaturated fluids, e.g., by forming reactive or non-reactive coatings on such surfaces. By way of example and without limitation, the biocompatible surface-active agent, either alone, or in combination with other such agents or other substances [e.g., undergoing surface adsorption with (e.g., in competition with or complexed with) such agents or such other substances], may be covalently or ionically bonded to a surface; immobilized thereupon; or otherwise adsorbed or deposited therewith to form such coatings. The improved characteristics may be imparted, for example, by placing one or more coatings (alone or in a multi-layered structure) on the fluid contacting surface (e.g., by dip-coating, by flushing a coating fluid from a pressurized source across the surface, etc.) for sufficient time for adsorption to occur.

The term "biocompatible surface-active agent" appearing herein means a substance forming a reactive or non-reactive coating on a fluid-contacting surface. Examples of biocompatible surface-active agents which may be used according to certain aspects of this invention include, by way of example and without limitation, a negatively charged moiety; a positively charged moiety; both a negatively charged moiety and a positively charged moiety; any biocompatible molecular entity that mitigates a high surface energy of a gas-supersaturated fluid delivery path (e.g., by promoting charge neutralization or surface free energy reduction); a protein; a globular protein; a structural protein; a membrane protein; a cell attachment protein; a glycoprotein; dipalmitoyl phosphatidylcholine (DPPC); a DPPC derivative; phosphorylcholine (PC); a mucous agent; a glycolated mucin; a polysaccharide; a surfactant; a nonproteolytic surfactant; a biocompatible surfactant; a glycosaminoglycan (GAG); a quaternary ammonium salt; stearalkonium; tridodecylmethyl ammonium chloride (TDMAC); benzalkonium; a biomolecule; heparin; a heparin salt; a water-soluble heparin salt; a water-insoluble heparin salt; cetyl trimethyl ammonium bromide (CTAB); and polyvinylpyrrolidone (PVP). In general, as used in the specification and claims, the term "biomolecule" means a material that is capable of engaging in a biological activity or that is capable of modulating a biological activity, either alone or in combination with different biomolecules, and combinations thereof. An example of a reactive coating including a biomolecule is a heparin coating. An example of a non-reactive coating is a PVP coating.

The term "gas-supersaturated fluid" appearing herein means a fluid in which the dissolved gas content would occupy a volume of between about 0.5 and about 3 times the volume of the solvent normalized to standard temperature and pressure. Examples of solvents which may be used include physiologic saline, lactated Ringer's, and other aqueous physiologic solutions. For medical applications, particularly advantageous gas-supersaturated fluids include oxygen-supersaturated fluids, although fluids including dissolved gases other than oxygen also may be used.

Compared to the fluids typically used clinically today, gas-supersaturated fluids are gas-enriched fluids including increased amounts of a dissolved gas. It is thought that gas-supersaturated fluids are "metastable" in that, as compared to clinically-used fluids, there is an increased potential for dissolved gas to come out of solution. For example, particles such as dust, debris, etc. generally do not affect the dissolved gas of clinically-used fluids as the gas remains in a dissolved state in the presence of such particles. However, with gas-supersaturated fluids, such particles may interefere with, disrupt, create or otherwise intereact with gas nuclei that seed bubble formation, growth or coalescence.

For example, one way of delivering gas-supersaturated fluids is via a glass capillary. However, borosilicate glasses contain negatively charged groups that impart a high surface energy to the surface contacting the gas-supersaturated fluid. It is thought that this high surface energy tends to attract and bind particles such as dust, debris, etc. that may promote bubble formation when gas-supersaturated fluids are passed through the capillary.

In applications where gas-supersaturated fluids are infused directly into a patient, and in applications where such fluids first are mixed with other fluids for such infusion, it is desirable to minimize, inhibit or eliminate physicochemical transitions (e.g., the emergence or growth of gas bubbles in the infused fluid) that might possibly result in undesirable physiologic responses by the patient. Such responses may be immediate or delayed, depending upon the circumstances involved in the physicochemical event(s) (e.g., the rate at which gas bubbles grow or coalesce). Accordingly, a simple and convenient way of minimizing, inhibiting, or eliminating undesirable physicochemical activity, particularly non-reactive physiochemical activity, associated with surfaces contacting gas-supersaturated fluids may be desirable.

The present invention may address one or more of the problems set forth above. Certain possible aspects of the present invention are set forth below as examples. It should be understood that these aspects are presented merely to provide the reader with a brief summary of certain forms the invention might take and that these aspects are not intended to limit the scope of the invention. Indeed, the invention may encompass a variety of aspects that may not be set forth below.

The present invention may include within its scope methods including the step of using biocompatible surface-active agents to impart improved characteristics to a surface contacting a gas-supersaturated fluid. The present invention also may include, by way of example and without limitation, methods including the step of forming a coating on a surface contacting gas-supersaturated fluids to impart improved characteristics to the surface, the coating including a biocompatible surface-active agent; methods including the step of providing a surface contacting gas-supersaturated fluids including a biomolecule coating imparting improved characteristics to the surface for such contacting; and methods including the step of coating a surface with heparin to impart improved characteristics to the surface for contacting gas-supersaturated fluids.

As used in the specification and claims, the term "medical device" means a device including a surface contacting gas-supersaturated fluid in the course of its operation, which fluid is used in a patient diagnostic or therapeutic procedure. This definition includes within its scope both blood contact and non-blood contact surfaces. This definition also includes within its scope devices for intravascular use, such as catheters, guidewires, and the like which may be placed into blood vessels or the heart, or proximate the heart, the brain, or other organs or tissues, and other devices, such as oxygenators, pumps, sensors, tubing, accumulators, capillaries, etc., which may be used either alone or in combination with such devices, advantageously for diagnostic or therapeutic purposes.

The present invention may be susceptible to various modifications and alternative forms. Specific embodiments of the present invention are described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

DETAILED DESCRIPTION OF SPECIFIC EMBODIMENTS

The description below discusses exemplary embodiments of the present invention. For the sake of clarity, not all features of an actual implementation of the present invention are described in this specification. It should be appreciated that in connection with developing any actual embodiment of the present invention many application-specific decisions must be made to achieve specific goals, which may vary from one application to another. Further, it should be appreciated that any such development effort might be complex and time-consuming, but would still be routine for those of ordinary skill in the art having the benefit of this disclosure.

A method is provided for coating medical device surfaces contacting gas-supersaturated fluids. One such medical device having such a surface comprises a capillary assembly, advantageously including a single fused silica capillary having a 100 $\mu$m inner diameter and a 350 $\mu$m outer diameter. Alternately, the capillary assembly may comprise a plurality of capillaries having inner diameters in the range of about 20 $\mu$m to about 1000 $\mu$m, with an inner diameter of about 100 $\mu$m to about 125 $\mu$m being particularly advantageous. The capillaries advantageously may be potted together or otherwise joined at their outer surfaces to form a single capillary bundle. The capillaries also may be formed of glass, PEEK (poly ether ether ketone) or another biocompatible material.

To coat the interior surface of a capillary assembly (e.g., one or more silica glass capillaries having a 100 $\mu$m inner diameter (commercially available from Polymicro, Calif.), a commercial preparation of benzalkonium chloride (BKC) and porcine intestine heparin (H) may be used at an 80 units/ml concentration in isopropyl alcohol (IPA). The capillary assembly advantageously is cleaned prior to being coated with the BKH solution. Cleaning may include the steps of flushing the capillary assembly with filtered water, ethanol or other solvents to remove debris and contaminants. Advantageously, the capillary assembly is polished and maintained in a particle-free environment.

To coat the capillary assembly, approximately forty tube volumes of ethanol are flushed through the capillary assembly, advantageously wetting the inner surface of each tubule. A solution of approximately 80 units/ml BKH in 99.99% pure IPA then is flushed through the capillary in an amount comparable with forty tube volumes. The IPA then is evaporated by filtered air flush.

Silica capillaries coated with BKH exhibited an increased ability to deliver oxygen-supersaturated fluids without bubble formation or growth as compared to clean but uncoated capillaries and to cleaned capillaries coated only with BKC. As shown in Table 1, no bubbles were observed when oxygen-supersaturated fluid was delivered at a flow rate of 2.0 ml/min through BKH coated capillaries into a beaker of still water. Uncoated capillaries, and capillaries coated with BKC only, did not exhibit such performance, and had a much higher incidence of failure, defined by the observance of microbubbles during testing.

TABLE 1

| Surface Preparation | No. Tested | No. Bubble-Free | % Not Bubble-Free |
|---|---|---|---|
| BKH | 10 | 10 | 0 |
| BKC | 15 | 12 | 20 |
| None | 10 | 7 | 30 |

The present invention has been described in terms of exemplary embodiments. In accordance with the present invention, the parameters for the methods disclosed may be varied, typically for a specific desired clinical indication. Further, it is contemplated that other embodiments, which may be devised readily by persons of ordinary skill in the art based on the teachings set forth herein, may be within the scope of the invention which is defined by the appended claims. The present invention may be modified and practiced in different but equivalent manners that will be apparent to those skilled in the art having the benefit of the teachings set forth herein.

No limitations are intended to the details shown herein, other than as described in the claims appended hereto. Thus, it should be clear that the specific embodiments disclosed above may be altered and modified, and that all such variations and modifications are within the spirit and scope of the present invention as set forth in the claims appended hereto.

What is claimed is:

1. A method of delivering gas-supersaturated fluid, the method comprising the act of:
   passing the gas-supersaturated fluid through a portion of a delivery device having a surface comprising a biocompatible surface-active agent.

2. A method of delivering gas-supersaturated fluid, the method comprising the acts of:
   (a) providing a delivery device, a portion of the delivery device having a surface comprising a biocompatible surface-active agent; and
   (b) passing the gas-supersaturated fluid across the surface.

3. The method of claim 2, wherein the biocompatible surface-active agent comprises a biomolecule.

4. The method of claim 3, wherein the biomolecule is immobilized.

5. The method of claim 3, wherein the biomolecule comprises heparin.

6. The method of claim 5, comprising the step of binding the heparin by a moiety to the surface through an ionic bond.

7. The method of claim 6, wherein the moiety comprises benzalkonium chloride.

8. The method of claim 5, comprising the step of binding the heparin by a moiety to the surface through a covalent bond.

9. The method of claim 2, wherein the surface forms a portion of a medical device.

10. The method of claim 9, wherein the medical device comprises an assembly for supplying a gas-supersaturated fluid.

11. The method of claim 9, wherein the medical device comprises an assembly for supplying an oxygen-supersaturated fluid.

12. The method of claim 11, wherein the oxygen-supersaturated fluid comprises physiologic saline.

13. The method of claim 2, wherein act (a) comprises the act of:
   coating the portion of the delivery device with the biocompatible surface-active agent to form the surface.

14. The method of claim 13, wherein the portion of the delivery device has a net negative surface charge.

15. The method of claim 13, wherein the portion of the delivery device comprises borosilicate glass.

16. The method of claim 2, wherein the portion of the delivery device comprises a capillary.

17. The method of claim 2, wherein the delivery device comprises a catheter.

18. The method of claim 2, wherein the delivery device comprises a guidewire.

19. The method of claim 2, wherein the delivery device comprises a tube.

20. The method of claim 2, wherein the biocompatible surface-active agent facilitates delivery of the gas-supersaturated fluid in a bubble-free manner.

21. The method of claim 2, wherein the biocompatible surface-active agent comprises heparin.

22. The method of claim 2, wherein the biocompatible surface-active agent comprises benzalkonium heparin.

23. The method of claim 2, wherein the gas-supersaturated fluid comprises an oxygen-supersaturated fluid.

24. The method of claim 2, wherein the gas-supersaturated fluid comprises fluid isotonic to blood.

25. The method of claim 2, wherein the biocompatible surface-active agent neutralizes a surface charge of the surface.

26. The method of claim 2, wherein the biocompatible surface-active agent reduces surface energy of the surface.

27. The method of claim 2, wherein a portion of the surface forms a tube.

28. The method of claim 2, wherein a portion of the surface forms a capillary.

29. The method of claim 2, wherein the biocompatible surface-active agent comprises a quaternary ammonium salt.

30. The method of claim 2, wherein the biocompatible surface-active agent imparts improved characteristics to the surface across which the gas-supersaturated fluid passes.

31. The method of claim 2, wherein act (a) comprises the act of: forming a coating on the surface to impart improved characteristics to the surface, the coating including the biocompatible surface-active agent.

* * * * *

UNITED STATES PATENT AND TRADEMARK OFFICE
CERTIFICATE OF CORRECTION

PATENT NO. : 6,533,766 B1  
DATED : March 18, 2003  
INVENTOR(S) : Patterson et al.

It is certified that error appears in the above-identified patent and that said Letters Patent is hereby corrected as shown below:

<u>Title page,</u>  
Item [75], Inventors, should read -- William R. Patterson, Irvin, CA (US); Jeffrey L. Creech, Marina Del Rey, CA (US), Paul J. Zalesky, Huntington Beach, CA (US) --.

Signed and Sealed this

Twelfth Day of August, 2003

JAMES E. ROGAN  
*Director of the United States Patent and Trademark Office*